(12) United States Patent
Alghamdi

(10) Patent No.: US 9,706,983 B1
(45) Date of Patent: Jul. 18, 2017

(54) METHOD FOR SUTURING SMALL SKIN WOUNDS

(71) Applicant: KING SAUD UNIVERSITY, Riyadh (SA)

(72) Inventor: Hussam Saeed Salem Alghamdi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/397,657

(22) Filed: Jan. 3, 2017

(51) Int. Cl.
*A61B 17/06* (2006.01)
*A61B 17/04* (2006.01)

(52) U.S. Cl.
CPC ........ *A61B 17/04* (2013.01); *A61B 17/06004* (2013.01); *A61B 17/06066* (2013.01); *A61B 17/0469* (2013.01); *A61B 17/06* (2013.01); *A61B 17/06166* (2013.01); *A61B 2017/0608* (2013.01); *A61B 2017/06019* (2013.01); *A61B 2017/06028* (2013.01); *A61B 2017/06052* (2013.01)

(58) Field of Classification Search
CPC ..... A61B 17/04; A61B 17/0469; A61B 17/06; A61B 17/06004; A61B 17/06066; A61B 17/06166; A61B 2017/06028
See application file for complete search history.

(56) References Cited

U.S. PATENT DOCUMENTS

| 4,092,739 | A | 6/1978 | Clemens et al. |
| 7,144,412 | B2 | 12/2006 | Wolf et al. |

FOREIGN PATENT DOCUMENTS

| RU | 2 352 271 C1 | 4/2009 |
| UA | 34 072 U | 7/2008 |

OTHER PUBLICATIONS

"Horizontal Mattress / Figure of 8 / Half Buried—Suture Techniques," Duke Suture Skills Course, You Tube website, published 2015.
Gunson, "Suturing techniques," DermNet NZ website, Dec. 29, 2013.

*Primary Examiner* — Robert Lynch
(74) *Attorney, Agent, or Firm* — Richard C. Litman

(57) ABSTRACT

The method for suturing small skin wounds includes providing a needle having a tip and an opposing trailing end, attaching a first end of a suture to the opposing trailing end, inserting the tip of the needle into the epidermis on a first side of the wound, extracting the needle from within an opposing second side of the wound, extracting the second end of the suture from within the first side of the wound, inserting the tip of the needle around the second end of the suture and into the first side of the wound, extracting the tip of the needle from the opposing second side of the wound to form a first loop, extracting the first end of the suture from within the second side of the wound to form a second loop, forming a knot in the suture, and tightening the knot to close the wound.

3 Claims, 12 Drawing Sheets

METHOD FOR SUTURING SMALL SKIN WOUNDS

BACKGROUND OF THE INVENTION

1. Field of the Invention

The present invention relates to surgical techniques, and particularly to a method for suturing small skin wounds.

2. Description of the Related Art

Sutures are typically used in surgical procedures to close surgical wounds, as well as to close the skin after a plastic surgery procedure, and to secure damaged or severed tendons, muscles or other internal tissues so as to support healing and regrowth. While loop stitching has been the primary procedure, particularly to close a surface wound, whether an accidental or surgical surface wound, looped sutures tend to leave very visible scars on the fully healed wound. Further, it can be very difficult to close small skin wounds under tension using the "near-far-far-near" suture, the dermal buried pulley suture, the modified buried dermal suturing, or the lateral pulley buried dermal suture. Although these techniques may be suitable for large wounds, these techniques can be very difficult to apply to small wounds, such as those associated with skin punch biopsies, as a result of the small diameter of the lesions versus the diameter of the suture needle. Moreover, controlling the tension can be aesthetically important as it prevents wound dehiscence and the widening of the scar.

Thus, a method for suturing small skin wounds solving the aforementioned problems is desired.

SUMMARY OF THE INVENTION

The method for suturing small skin wounds includes providing a needle having a tip and an opposing trailing end, attaching a first end of a suture to the opposing trailing end, inserting the tip of the needle into the epidermis on a first side of the wound, extracting the needle from within an opposing second side of the wound, extracting the second end of the suture from within the first side of the wound, inserting the tip of the needle around the second end of the suture and into the first side of the wound, extracting the tip of the needle from the opposing second side of the wound to form a first loop, extracting the first end of the suture from within the second side of the wound to form a second loop, forming a knot in the suture, and tightening the knot to close the wound.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
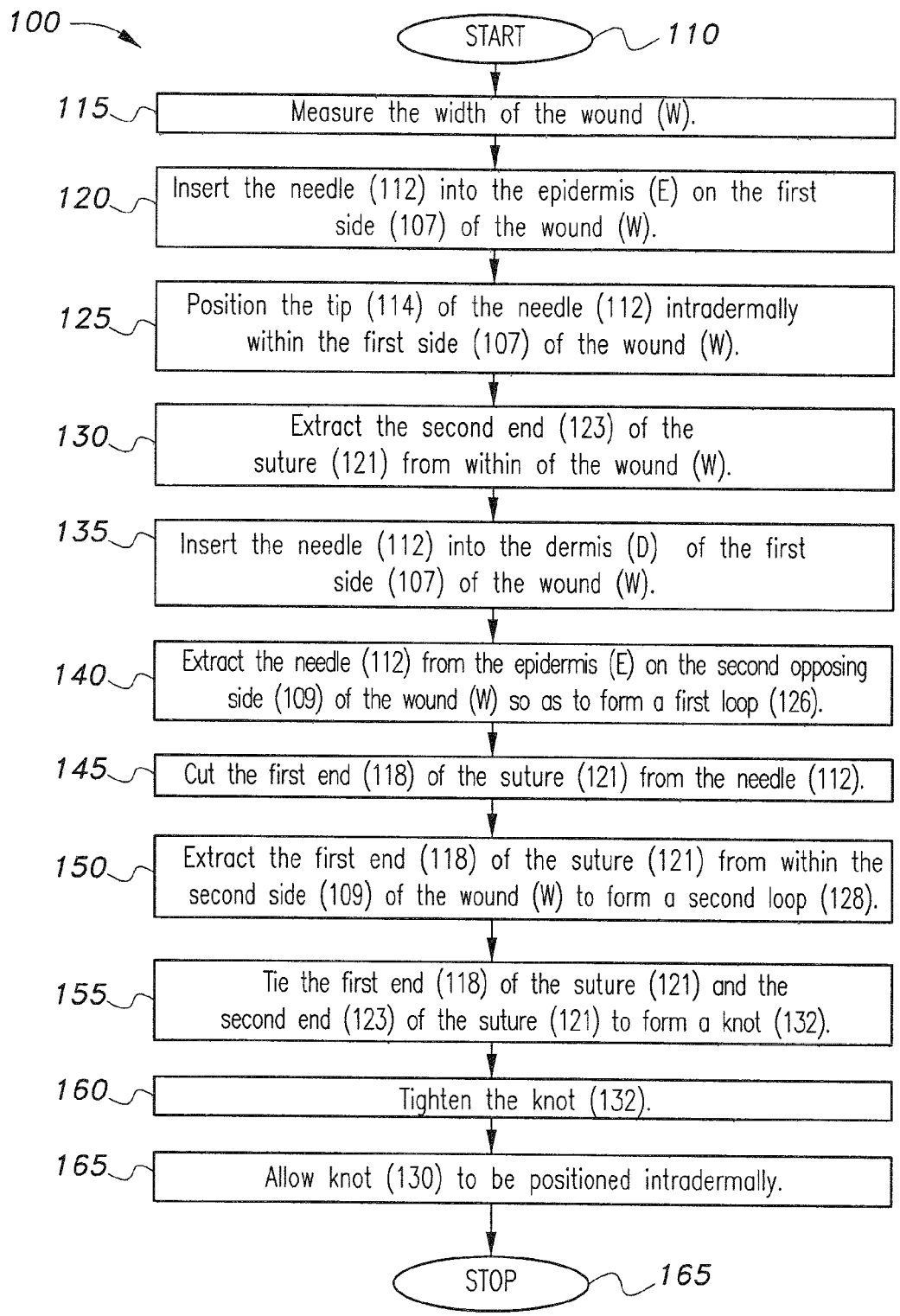
FIG. 1 is a flowchart illustrating the steps of a method for suturing a small skin wound according to the present invention.
Figure 2:
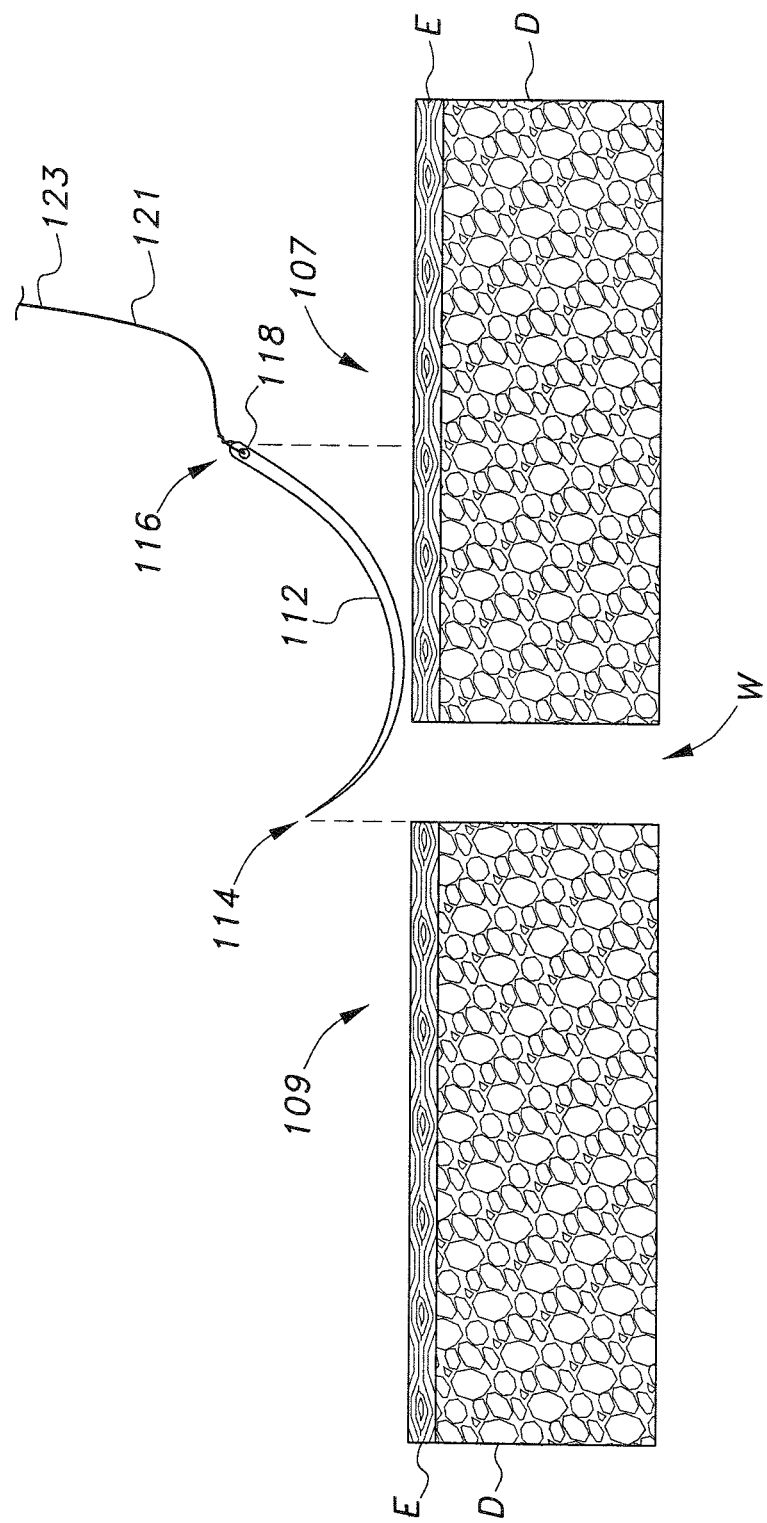
FIG. 2 is a diagrammatic side view in section depicting measuring a small skin wound.
Figure 3:
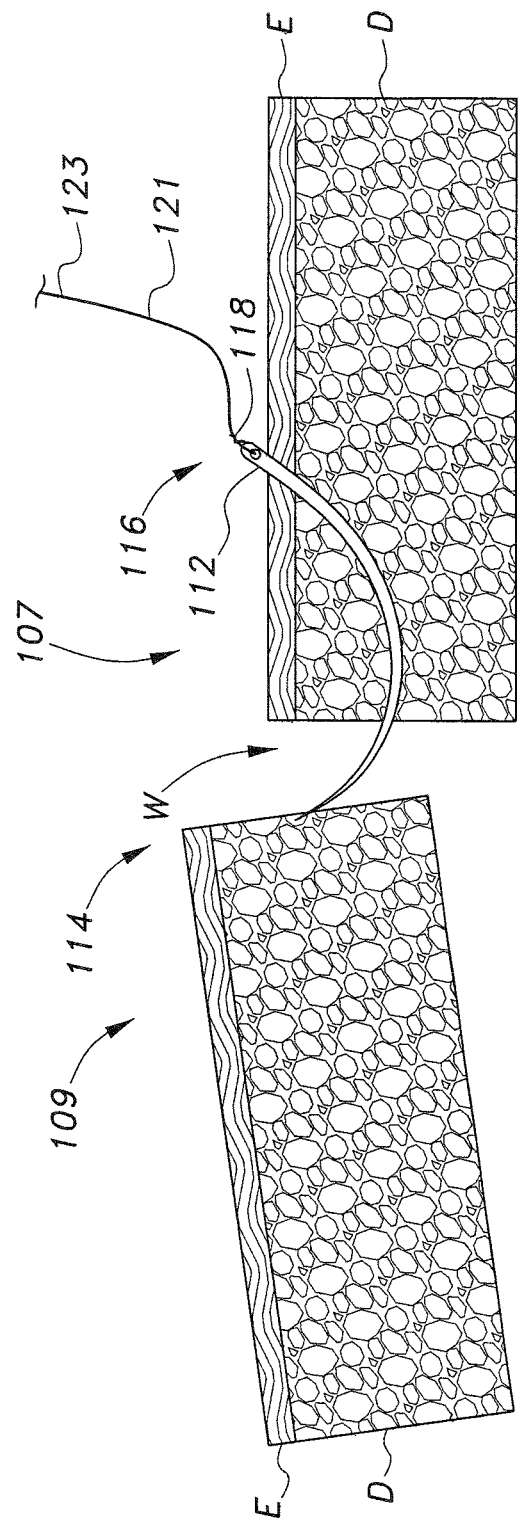
FIG. 3 is a diagrammatic side view in section illustrating the first step in a method for suturing a small skin wound according to the present invention.
Figure 4:
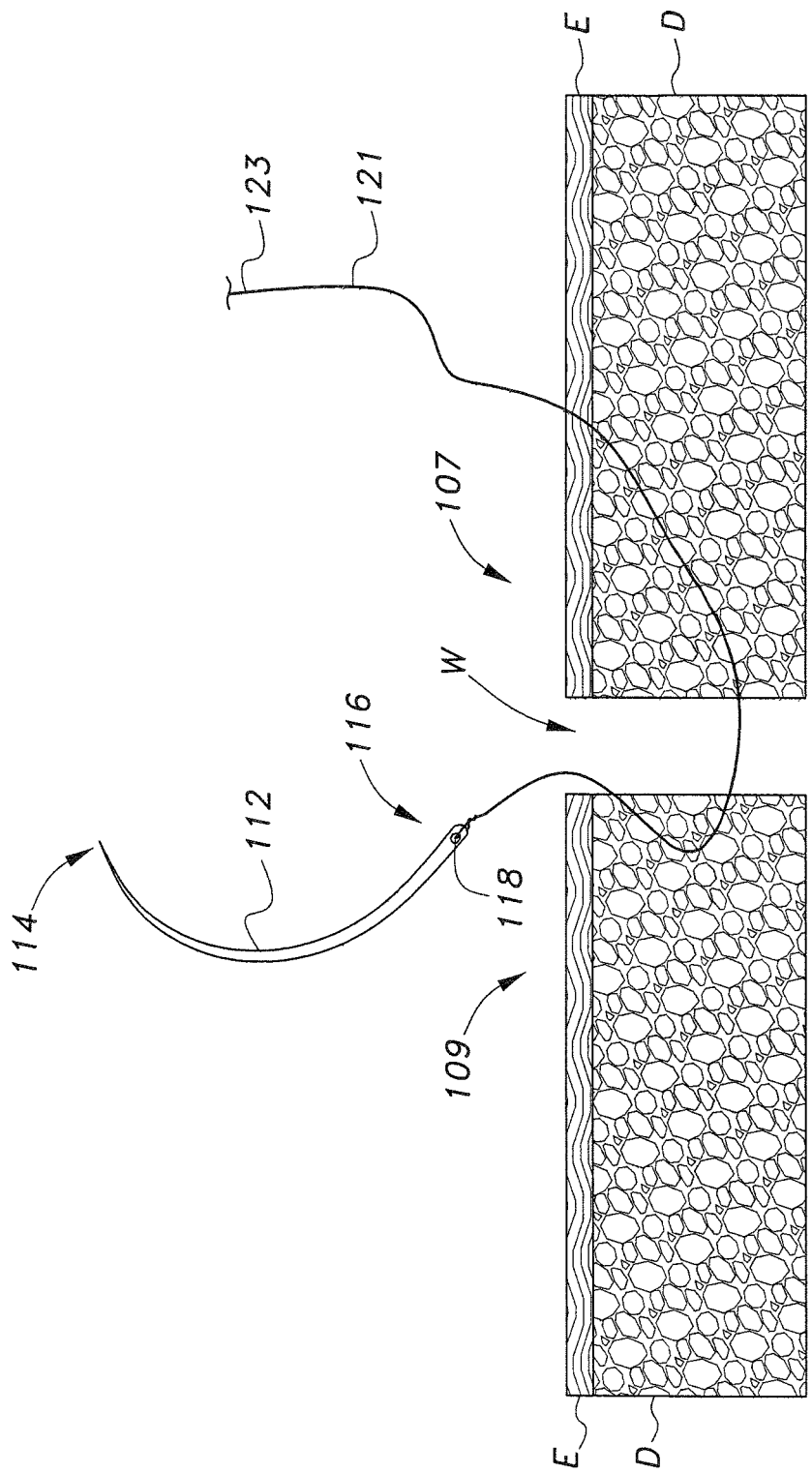
FIG. 4 is a diagrammatic side view in section illustrating the second step in a method for suturing a small skin wound according to the present invention.

FIGS. 1 through 12 illustrate a method 100 for suturing small skin wounds wherein the sutures are buried intradermally to improve the cosmetic appearance of the closed wound. To start (Step 110), a medical practitioner first measures the width of the wound W from a first side 107 (e.g., the right side) of the wound W to an opposing second side 109 (i.e., the left side) of the wound W with a needle 112, as illustrated in FIG. 2 (Step 115). The needle 112 includes a tip 114 and an opposing trailing end 116, a first end 118 of a suture 121 being attached to the opposing trailing end 116 of the needle 112. After the first end 118 of the suture 121 is attached to the opposing trailing end 116 of the needle 112, the practitioner inserts the tip 114 of the needle 112 into the epidermis E on the first side 107 of the wound W (Step 120) and positions the tip 114 of the needle 112 intradermally within the first side 107 of the wound W (Step 125). For example, the practitioner can insert the tip 114 of the needle 112 into the epidermis E of the first side 107 (i.e., the right side) of the wound W and position the tip 114 of the needle 112 intradermally within the second side 109 (i.e., the left side) of the wound W such that the tip 114 of the needle 112 does not pierce the epidermis E of the opposing second side 109 (i.e., the left side) of the wound W using a swinging motion going from down to up within the dermis D of the second side 109, as illustrated in FIGS. 3 and 4.

Figure 5:
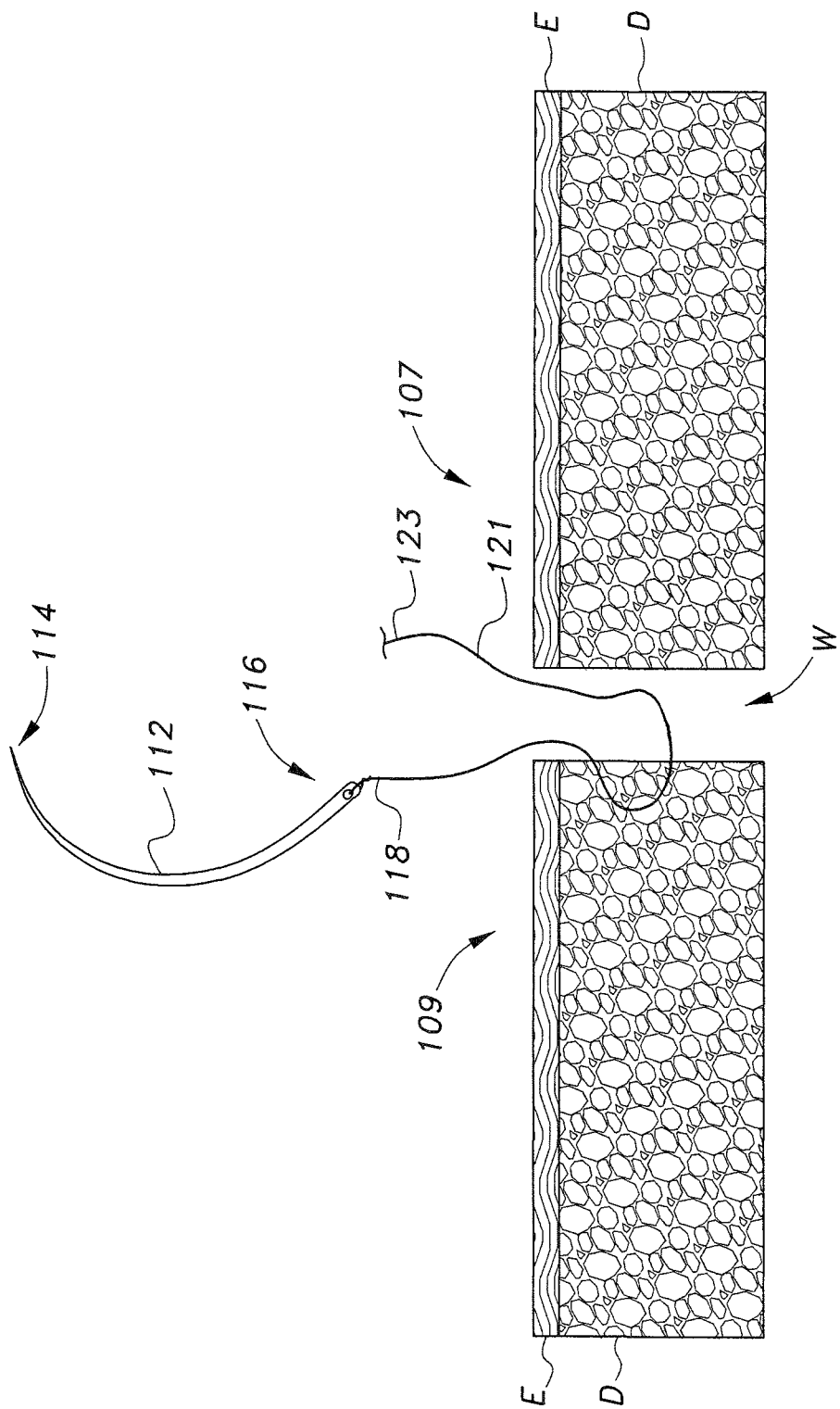
FIG. 5 is a diagrammatic side view in section illustrating the third step in a method for suturing a small skin wound according to the present invention.

The needle 112 can be extracted from the opposing second side 109 (i.e., the left side) of the wound W without piercing the epidermis E, as illustrated in FIG. 4, and extracts the second end 123 of the suture 121 from within the first side 107 (i.e., the right side) of the wound W (Step 130), as illustrated in FIG. 5. At this point the suture 121 is attached only to the dermis D of the second side 109, as illustrated in FIG. 5. It is to be understood that any suitable instrument, such as a hook H, can be used to extract the second end 123 from within the wound W.

Figure 6:
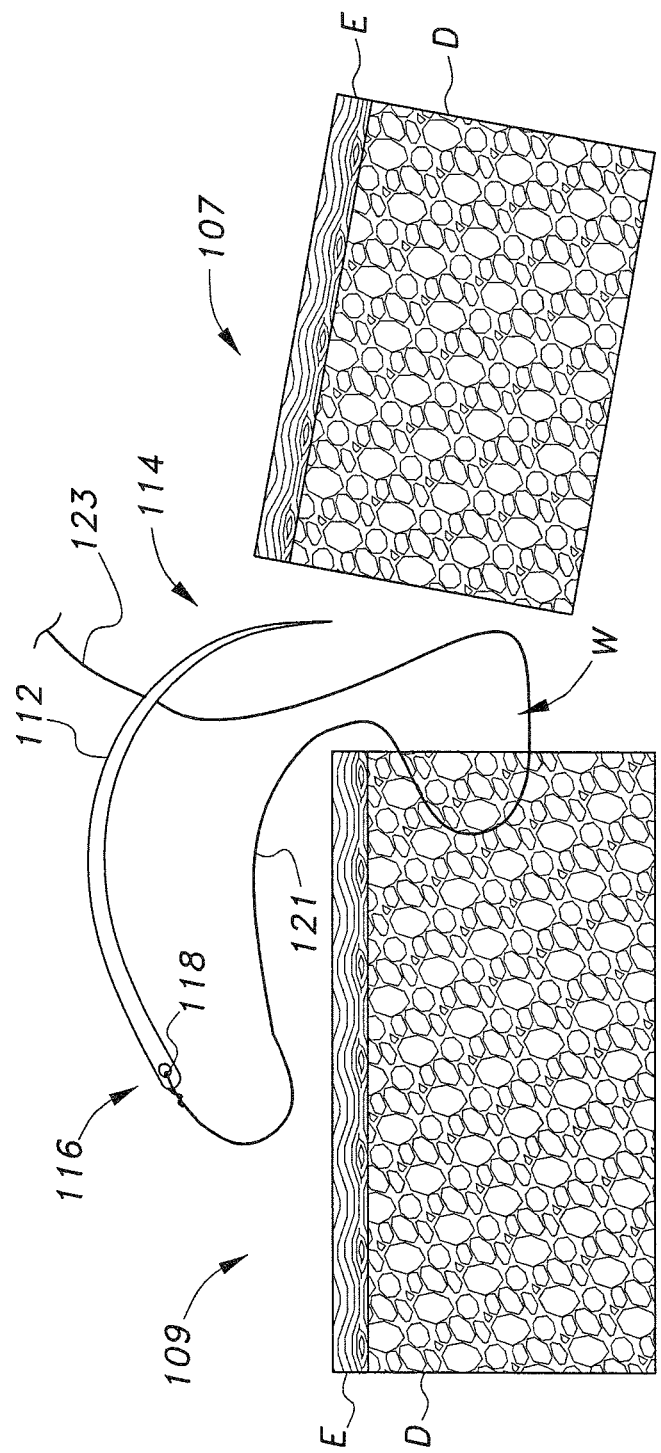
FIG. 6 is a diagrammatic side view in section illustrating the fourth step in a method for suturing a small skin wound according to the present invention.
Figure 7:
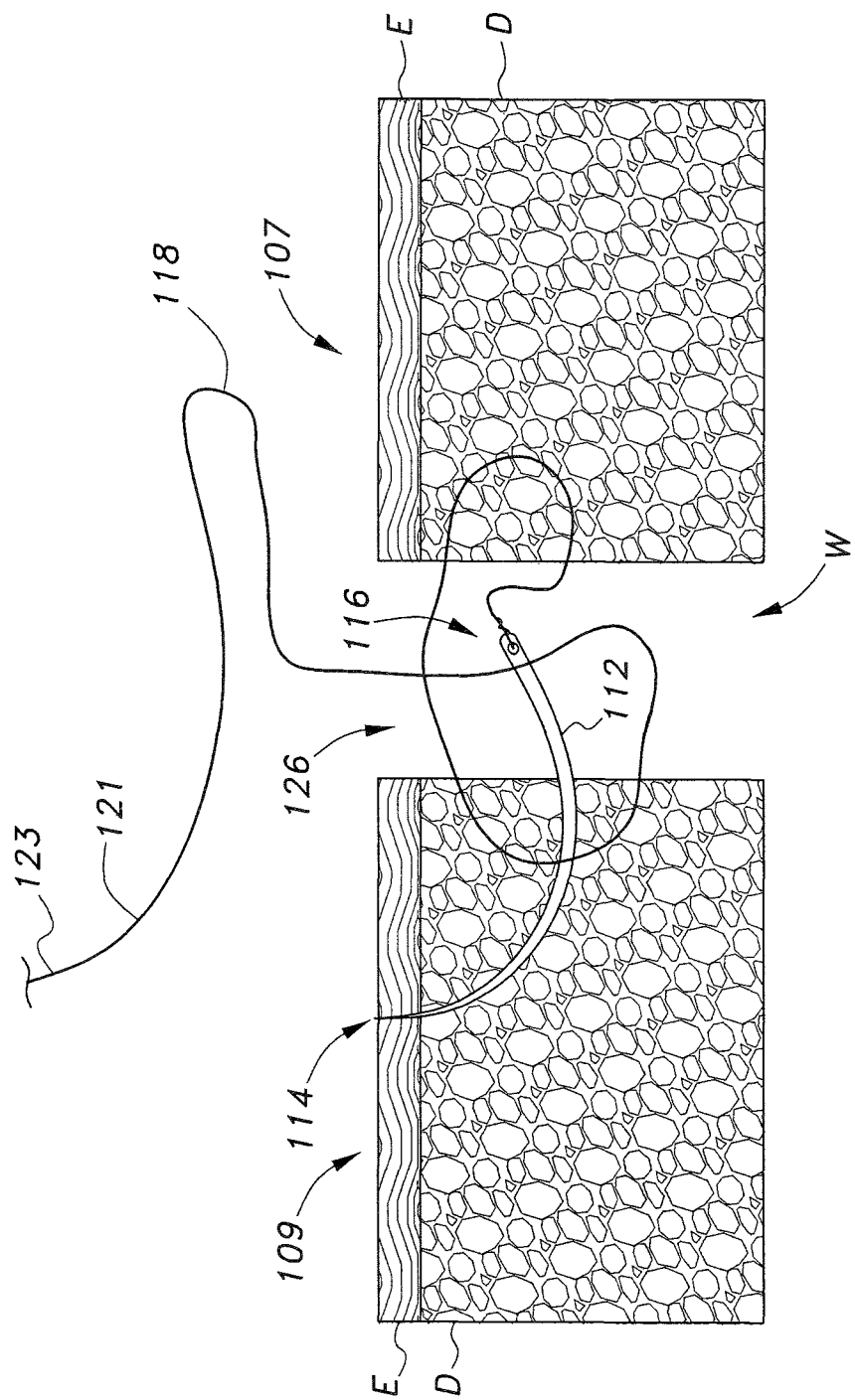
FIG. 7 is a diagrammatic side view in section illustrating the fifth step in a method for suturing a small skin wound according to the present invention.
Figure 8:
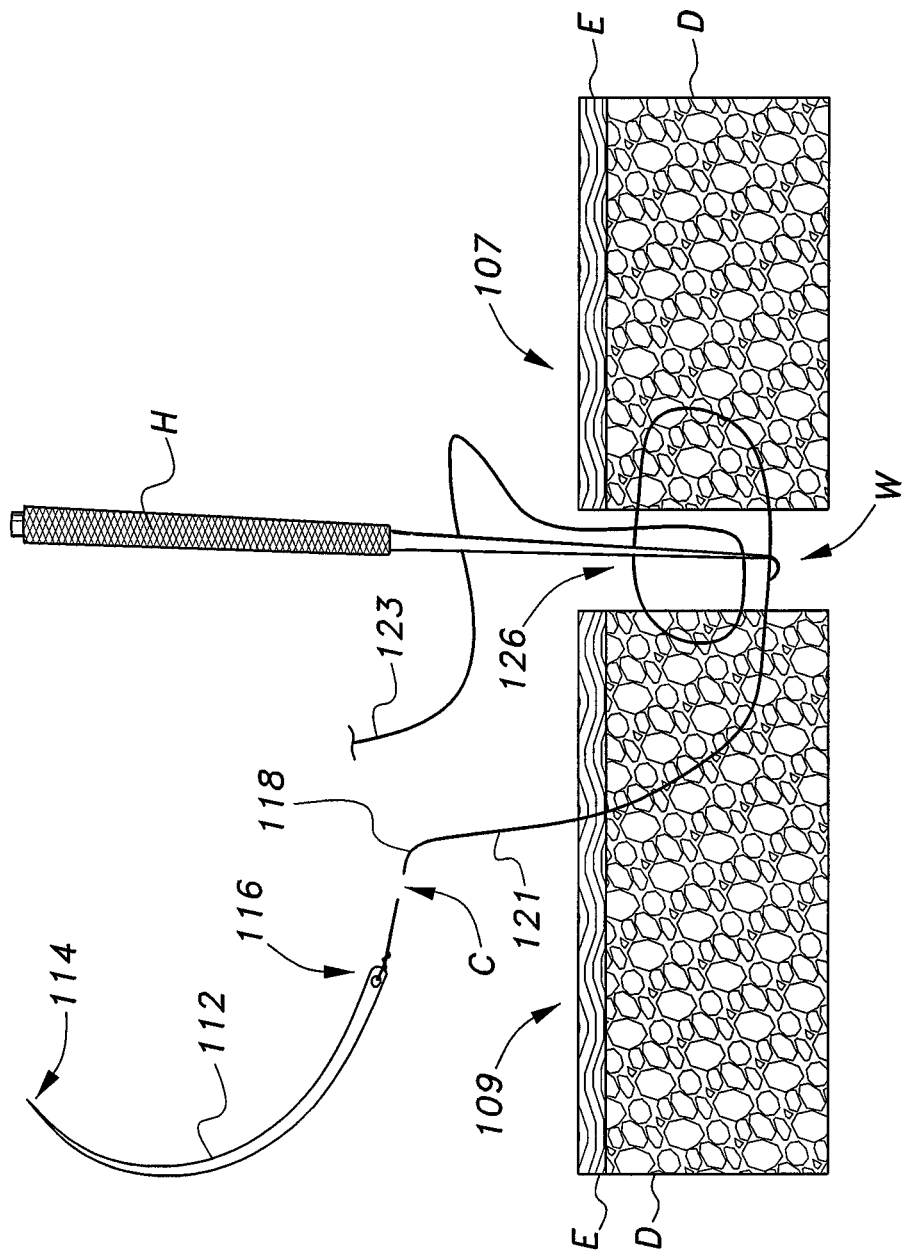
FIG. 8 is a diagrammatic side view in section illustrating the sixth step in a method for suturing a small skin wound according to the present invention.

The tip 114 of the needle 112 is then moved across the second end 123 of the suture 121 (Step 135) and inserted into the dermis D of the first side 107 (i.e., the right side) of the wound W, as illustrated in FIG. 6. After the tip 114 of the needle 112 is inserted into the dermis D of the first side 107 (i.e., the right side) of the wound W using a swing motion from up to down, the needle 112 is extracted from the epidermis E on the opposing second side 109 (i.e., the left side) of the wound W, to form a first loop 126 (Step 140), as illustrated in FIG. 7. The first end 118 of the suture 121 is then detached from the opposing trailing end 116 of the needle 112, e.g., using scissors at location C, (Step 145), as illustrated in FIG. 8. Once separated, the first end 118 of the suture 121 is extracted from within the second side 109 (i.e., the left side) of the wound W to form a second loop 128 (Step 150), as illustrated in FIG. 9.

Figure 9:
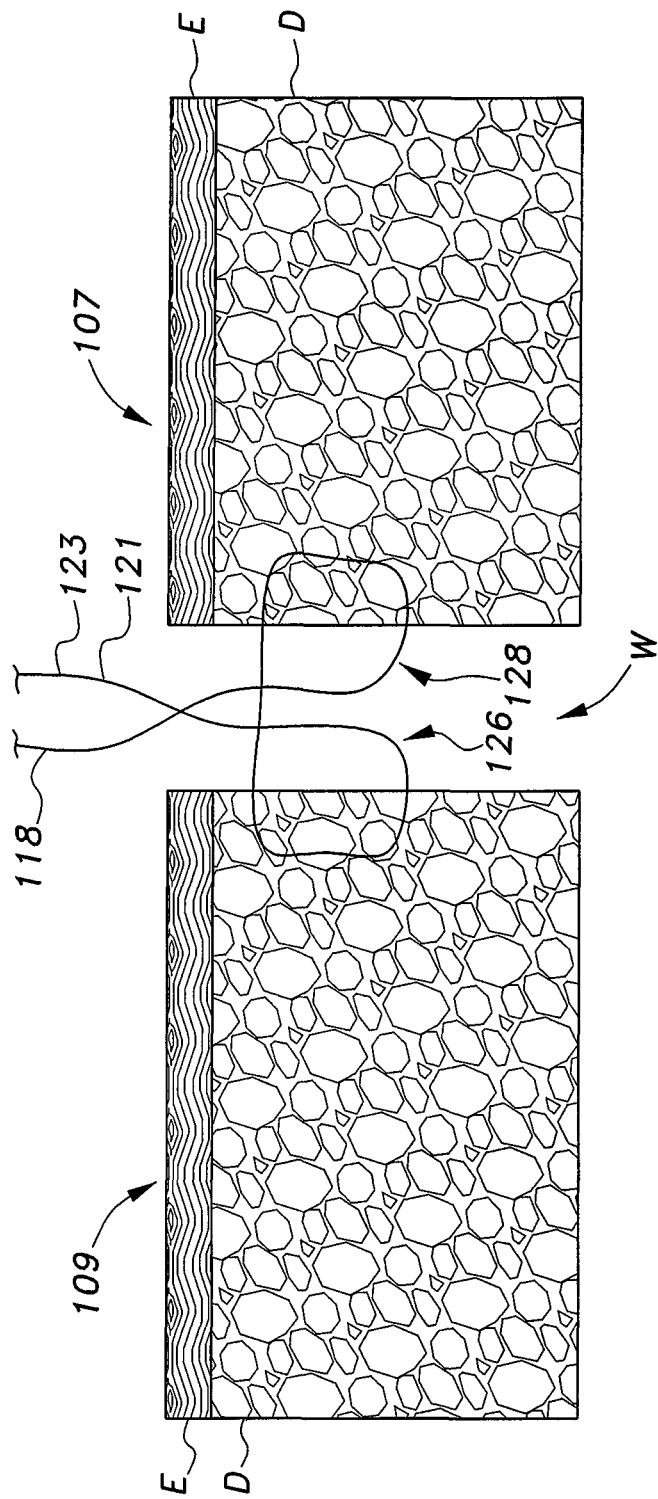
FIG. 9 is a diagrammatic side view in section illustrating the seventh step in a method for suturing a small skin wound according to the present invention.
Figure 10:
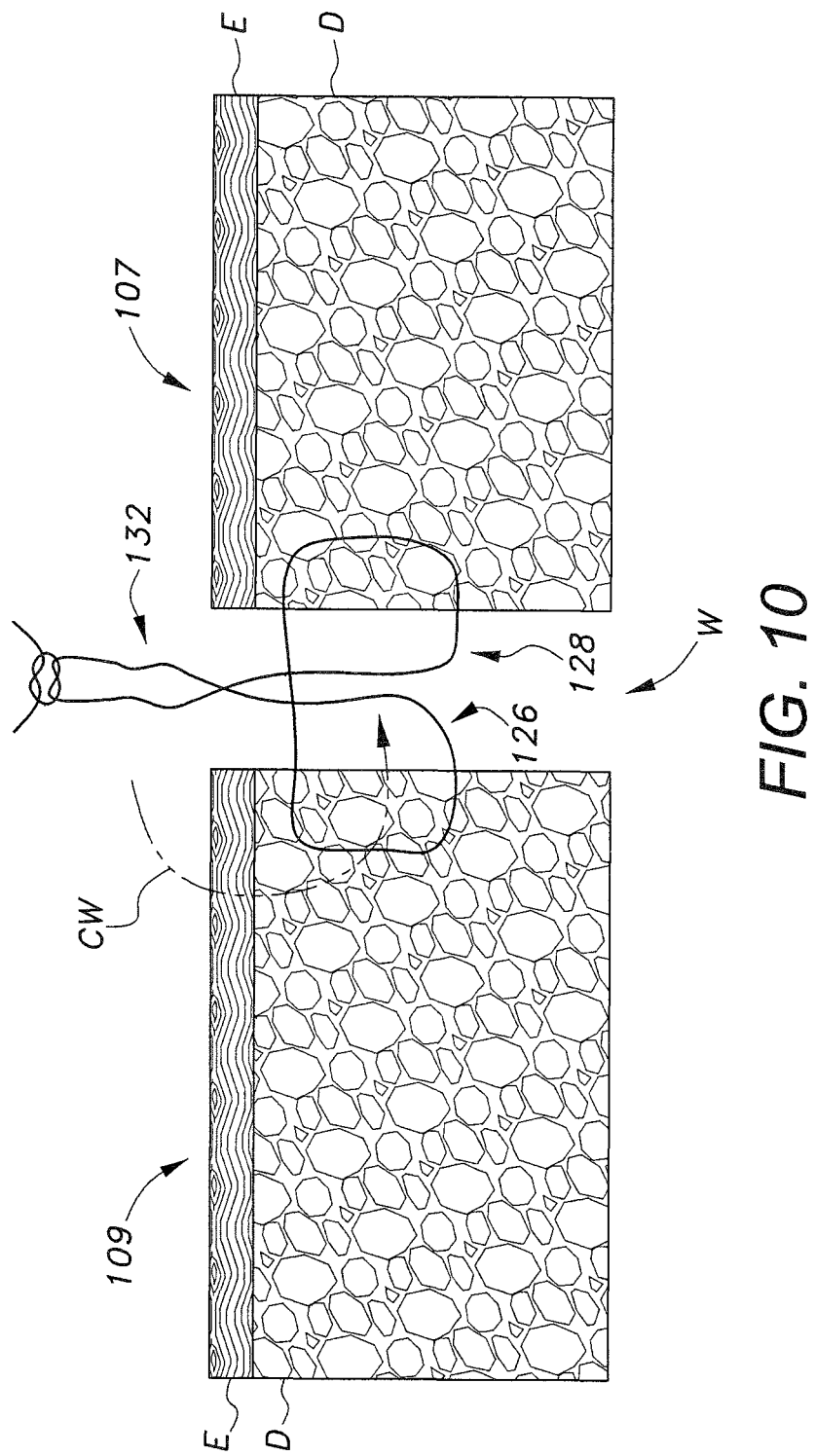
FIG. 10 is a diagrammatic side view in section illustrating the eighth step in a method for suturing a small skin wound according to the present invention.
Figure 11:
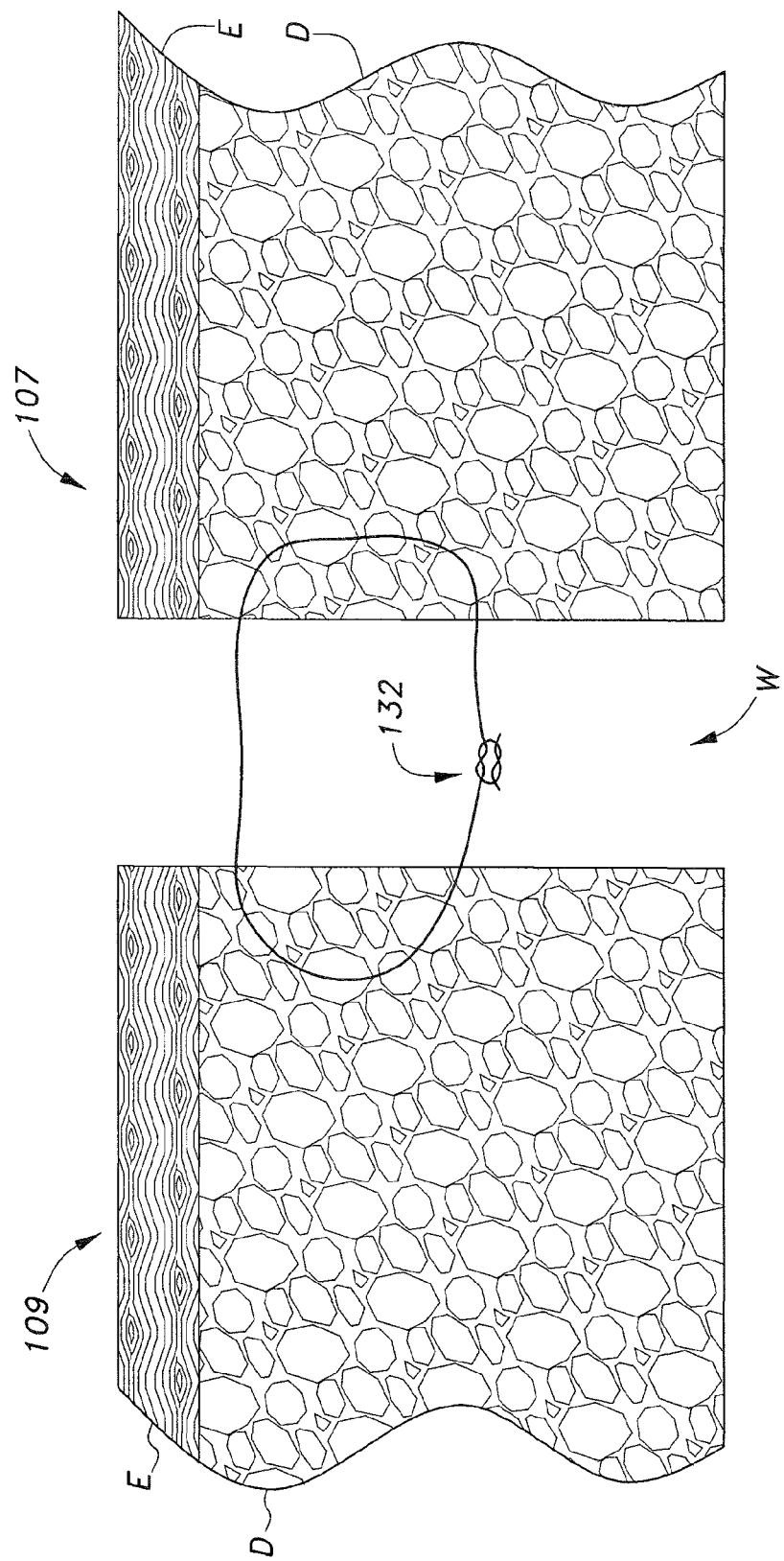
FIG. 11 is a diagrammatic side view in section illustrating the ninth step in a method for suturing a small skin wound, according to the present invention.
Figure 12:
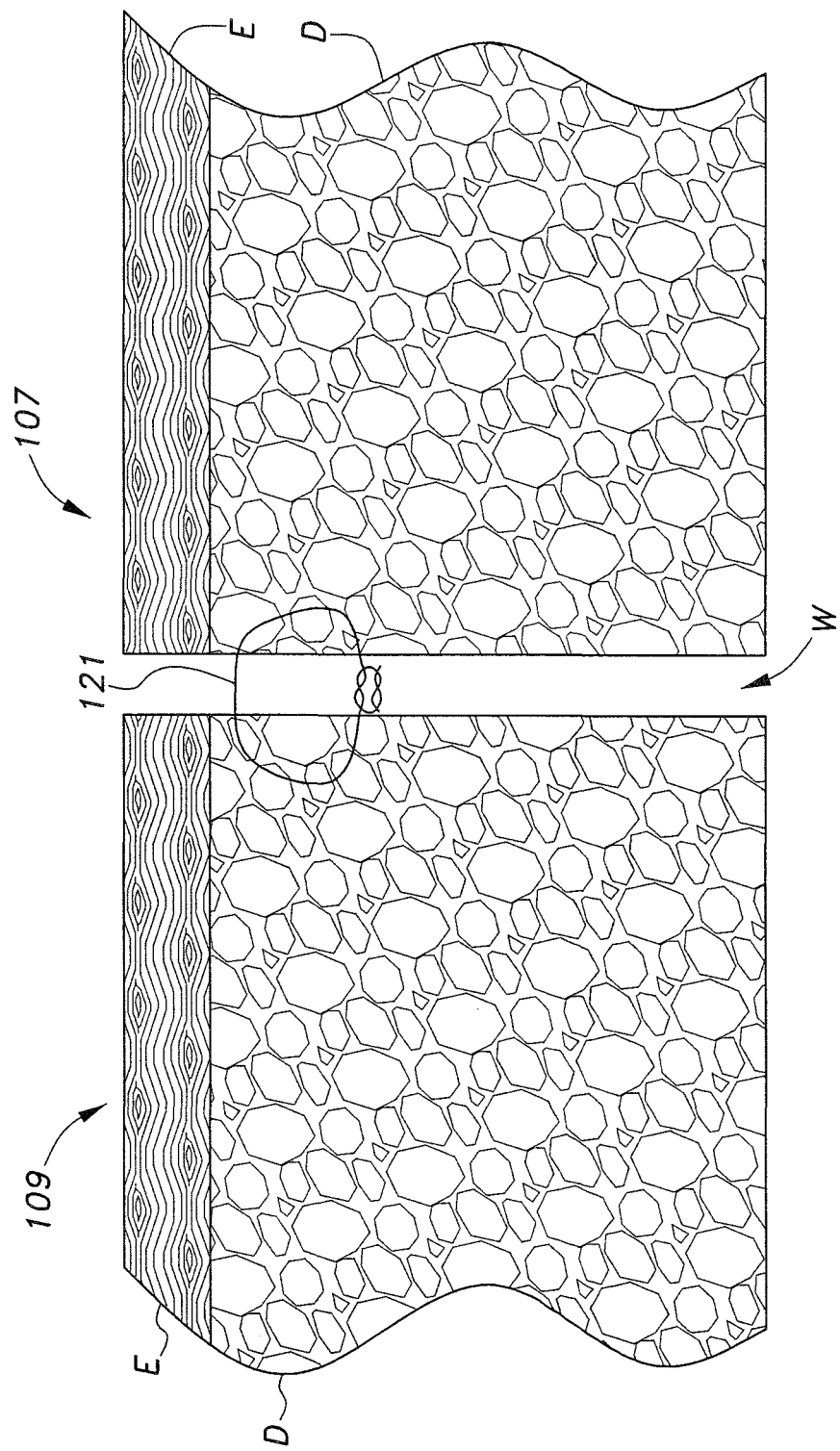
FIG. 12 is a diagrammatic side view in section illustrating the tenth step in a method for suturing a small skin wound according to the present invention.

Once both the first end 118 of the suture 121 and the second end 123 of the suture 121 cross one another outside of the wound W, as illustrated in FIG. 9, the first end 118 of the suture 121 and the second end 123 of the suture 121 can be tied together, such as along the long axis of the wound W, to form a knot 132, e.g., a square knot (Step 155), as illustrated in FIG. 10. The knot 132 is then tightened (Step 160) to bring the first side 107 of the wound W and the opposing second side 109 of the wound W together and allow the wound W to heal, as illustrated in FIG. 11. After tightening the knot 132, it may slide to its natural position deep within the wound W, as indicated by the arrow CW, (Step 165) because the two ends of the suture 118 and 123 are facing down within the wound W. In this position, the knot 132 can be hidden from view, as illustrated in FIG. 12. After the knot has been positioned intradermally, the procedure is complete (Step 170). It is to be understood that the practitioner can attach an adhesive bandage to cover the incisions on the epidermis E of the patient.

The needle 112 used to suture the wound W can be any type of suitable suture needle, such as a curved suture needle, as shown in FIGS. 2 through 11. The sutures can be any suitable type of sutures, such absorbable sutures form from any suitable material, such as polyglactin 910 (i.e., vicryl), polyglyconate, polydioxane, or poliglecaprone, or non-absorbable sutures formed from any suitable material, such as silk, nylon, polyester, polypropylene or cotton. Typically, surgeons prefer absorbable sutures that do not need to be removed for buried dermal sutures.

It is to be understood that the present invention is not limited to the embodiments described above, but encompasses any and all embodiments within the scope of the following claims.

I claim:

1. A method for suturing small skin wounds, comprising the steps of:
    providing a needle having a tip and an opposing trailing end;
    attaching a first end of a suture to the opposing trailing end of the needle;
    inserting the tip of the needle into the epidermis on a first side of the wound;
    positioning the tip of the needle intradermally within an opposing second side of the wound;
    extracting the needle from within the opposing second side of the wound;
    extracting an opposing second end of the suture from within the first side of the wound;
    inserting the tip of the needle around the second end of the suture into the first side of the wound;
    extracting the tip of the needle from the epidermis on the opposing second side of the wound to form a first loop;
    detaching the first end of the suture from the opposing trailing end of the needle;
    extracting the first end of the suture from within the second side of the wound to form a second loop;
    forming a knot in the suture; and
    tightening the knot to bring the sides of the wound together.

2. The method for suturing small skin wounds according to claim 1, further comprising the step of measuring the width of the wound.

3. The method for suturing small skin wounds according to claim 1, wherein the knot comprises a square knot.

* * * * *